Figure 1:
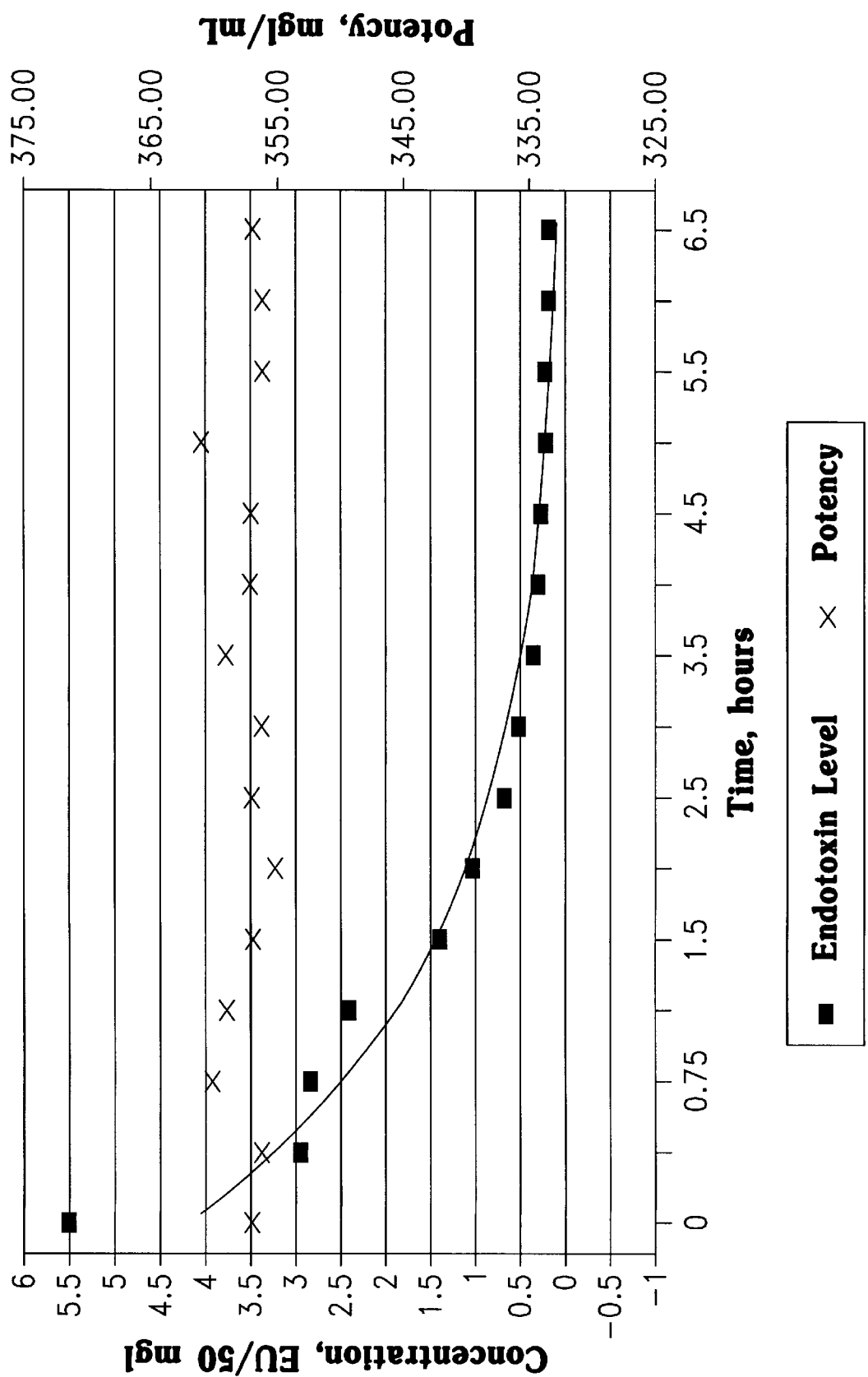

United States Patent
Karras et al.

[11] Patent Number: 5,972,225
[45] Date of Patent: Oct. 26, 1999

[54] PROCESS FOR REMEDIATING ENDOTOXIN-CONTAMINATED BULK NON-IONIC CONTRAST MEDIA

[75] Inventors: Lee Karras, Bloomington, Ind.; Barry Graham, North Blenheim, N.Y.

[73] Assignee: Cook Imaging Corporation, Bloomington, Ind.

[21] Appl. No.: 08/852,315

[22] Filed: May 7, 1997

Related U.S. Application Data

[60] Provisional application No. 60/016,768, May 7, 1996.

[51] Int. Cl.$^6$ ..................................................... B01D 15/00
[52] U.S. Cl. ............................................. 210/694; 422/41
[58] Field of Search ................................ 210/694; 422/1, 422/101, 102, 41

[56] References Cited

U.S. PATENT DOCUMENTS

| | | | |
|---|---|---|---|
| 4,059,512 | 11/1977 | Harris | 210/24 |
| 4,863,714 | 9/1989 | Sovak et al. | 424/5 |
| 4,885,168 | 12/1989 | Hashimoto et al. | 424/95 |
| 5,045,456 | 9/1991 | Rienstra et al. | 435/101 |
| 5,204,005 | 4/1993 | Doran, III et al. | 210/656 |
| 5,447,635 | 9/1995 | Viscardi et al. | 210/636 |

*Primary Examiner*—Ivars Cintins
*Attorney, Agent, or Firm*—Woodard, Emhardt, Naughton Moriarty & McNett

[57] ABSTRACT

A novel process for selectively removing endotoxin from an aqueous solution containing bulk, iodinated, non-ionic contrast media and endotoxin by passing the solution through an activated carbon filter. The process can be economically practiced on a factory scale.

20 Claims, 1 Drawing Sheet

PROCESS FOR REMEDIATING ENDOTOXIN-CONTAMINATED BULK NON-IONIC CONTRAST MEDIA

This application claims the benefit of U.S. Provisional Application No. 60/016,768, filed May 7, 1996.

BACKGROUND OF THE INVENTION

This invention relates to the remediation of endotoxin-contaminated bulk, iodinated non-ionic contrast media. More particularly, the invention pertains to a process for removing endotoxin from such bulk contrast media.

As further background, medical imaging has come to depend to a great extent upon radiographic contrast media. In the X-ray visualization of relatively extensive regions of the human body, for example the cardiovascular system or the space containing the cerebrospinal fluid, large quantities of X-ray contrast agents of high concentration must be injected in order to provide sufficient opacity in the region concerned to produce a clear X-ray image.

As the technology surrounding the production of contrast media has advanced, a problem which has arisen relates to the presence of endotoxins which are produced by bacterial proliferation during the handling of large quantities of aqueous solutions. While the bacteria themselves are easily destroyed in various sterilization procedures, endotoxins are at times left intact.

In this regard, endotoxins have been known and studied for many years particularly in regard to the pathophysiological reactions in animals. For many years it was believed that endotoxin material was contained within gram-negative bacilli cells and was released only upon disintegration of the cell walls. Hence, the material was termed endotoxin. Recent studies, however, suggest that endotoxin is localized at the cell surface of gram-negative bacilli and may be present with viable and killed cells as well as in a free form within a liquid medium.

Endotoxins are known to cause several and varied pathophysiological reactions and have been identified as direct and contributory causes of death of many hospitalized patients. Endotoxins are known to cause febrile reactions in animals with symptoms of extremely high fever, vasodilation, diarrhea, and the like and, in extreme cases, fatal shock. It is also known that endotoxins cause leucocytosis, deleterious changes in carbohydrate and protein metabolism and widespread intravascular clotting by fibrin formation.

Studies have shown that endotoxemia in animals may be caused by gram-negative bacilli primary and secondary infections and/or the employment of intravenous apparatus or solutions contaminated with gram-negative bacilli or endotoxin. The occurrence of endotoxemia from the use of endotoxin-contaminated intravenous or parenteral solutions has recently been recognized as a particular problem in modern hospitals. Since contrast media are often injected into hospital patients in large quantities, the contrast media must first be purified of endotoxin contanimation.

It is presently a common practice in the medical profession to counteract endotoxemia by treatment with massive infusions of antibiotics. However, it has not been shown that antibiotics remove endotoxin other than by controlling gram-negative bacilli. Removal of the bacilli solves the problem of endotoxin production; however, it does nothing to remove the endotoxin that already exists in solution.

In light of this background there exists a need for fast and cost-effective ways to remediate endotoxin-contaminated bulk non-ionic contrast media. The present invention addresses this need.

SUMMARY

It has been discovered that bulk non-ionic iodinated contrast media which is found to have an excessively high level of endotoxin can be reconstituted in aqueous solution and remediated by a process which includes continuously and repeatedly passing the aqueous solution through a filtration zone containing activated carbon, and further, that the resulting solution can be taken immediately to formulation thus avoiding the need to undergo tedious recrystallizations which may result in product loss. Accordingly, one preferred embodiment of the present invention provides a process for remediating a bulk, non-ionic iodinated contrast agent which comprises dissolving the agent in an aqueous solution. The solution is then continuously and repeatedly passed through a filtration zone containing activated carbon, for a duration and under conditions effective to produce a product solution of the agent which is essentially free from endotoxin.

Another preferred embodiment of the invention provides a process for producing a formulated, non-ionic iodinated contrast medium from an endotoxin-contaminated bulk non-ionic iodinated contrast medium. The process includes the steps of:

(a) dissolving an amount of a solid endotoxin-contaminated bulk non-ionic iodinated contrast agent in aqueous solution;

(b) continuously and repeatedly passing said aqueous solution from step (a) through a filtration zone containing activated charcoal for a duration and under conditions effective to adsorb essentially all of said endotoxin on said activated charcoal and produce a production solution essentially free from endotoxin;

(c) filling the product solution from step (b) into sterilizable containers; and (d) sterilizing filled containers from step (c).

According to one preferred form of the invention, a solid, bulk, endotoxin-contaminated contrast medium is dissolved in aqueous solution and placed in a holding tank fluidly coupled to a purification system. This system includes a pump and an in-line activated carbon filter. The aqueous solution is continuously pumped from the holding tank into the purification system and after passage through the activated carbon filter the solution is deposited back into the holding tank. In the preferred process the volume of the purification system is small relative to that of the holding tank. In this manner, the system can be run continuously over a period of time with no additional steps required for effective remediation of the contaminated batch.

Processes of the invention are applied with preference to non-ionic iodinated contrast media of the following formula:

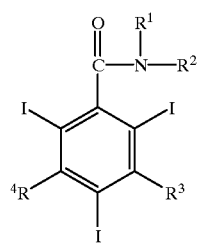

wherein $R^1$ and $R^2$, which may be the same or different, are each a hydrogen atom, an alkyl group, a hydroxylalkyl group or an alkanoyloxyalkyl group and $R^3$ and $R^4$ which may be the same or different, are each a group of the formula—$NR^5Ac$, where $R^5$ is a hydrogen atom, an alkyl group, a hydroxylalkyl group, an alkanoyloxyalkyl group or an alkanoyl group and Ac is an alkanoyl group; a group of the formula—$CH_2NR^5Ac$, where $R^5$ and Ac have the above meanings; or a group

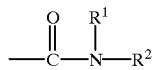

as defined above; each alkyl, hydroxyalkyl or alkanoyl group which is present having up to 6 carbon atoms there being at least one N-hydroxyalkyl and at least two hydroxyl groups in the molecule.

Processes of the invention are most preferably applied to the non-ionic iodinated contrast medium Ioxilan, i.e. 5-(N (2,3-dihydroxypropyl) acetamido) N-(2-hydroxyethyl)-N'- (2,3-dihydroxypropyl) 2,4,6-triiodo-isophthalamide.

Processes of the invention reliably remove endotoxins from endotoxin-contaminated, bulk non-ionic iodinated contrast media. The inventive processes can be utilized at the pre-drug product stage and results in no damage to or significant loss of product. It has been found that the activated carbon selectively binds the endotoxins and allows passage of the contrast media without affect on the media or fouling of the activated carbon.

An object of the invention is to provide a process for the removal of endotoxins from bulk non-ionic contrast media which can be readily and inexpensively performed using conventional equipment.

Another object of the invention is to provides a process which result in aqueous solutions which be taken directly to formulation and sterilization without the need for intermediate recrystallization of the contrast agent.

Additional objects, features and advantages of the invention will be apparent from the following description.

DESCRIPTION

For the purpose of promoting an understanding of the principles of the invention, reference will now be made to the certain embodiments thereof and specific language will be used to describe the same. It will nevertheless be understood that no limitation of the scope of the invention is thereby intended, such alterations and further modifications, and such further applications of the principles of the invention therein being contemplated as would normally occur to one skilled in the art to which the invention applies.

Novel processes are provided for removing endotoxins from bulk non-ionic iodinated contrast media. In this regard, the term "bulk" as used herein is intended to mean a product prior to formulation which is essentially free from impurities other than endotoxins. Thus, generally speaking, the bulk non-ionic iodinated contrast media will meet specifications relating to other impurities, but will contain excessively high levels of endotoxin.

As is known, the term "endotoxin" refers to a complex lipopolysaccharide material derived from gram-negative bacilli that is known to produce a wide variety of pathophysiological reactions in animals. Studies have demonstrated that endotoxin is distinguishable from classic protein toxins due to its failure to be neutralized by anti-serum, its increased heat stability and its failure to be converted to toxoid by treatment with formaldehyde. Moreover, endotoxin exhibits a lesser degree of potency than classic protein toxins and produces essentially similar reactions in animals regardless of the microbial origin of the endotoxin.

The complex lipopolysaccharide material commonly identified as endotoxin may be derived from gram-negative bacilli including, by way of example, the Escherichia, Klebsiella, Proteus, Pseudomonas, Salmonella, Citrobacter, Bordetella, Serratia and Shigella types, to name a few. Endotoxins derived from different types of gram-negative bacilli are typically essentially the same in biochemical composition and structure and produce essentially similar reactions in animals.

The solution to be treated in accordance with the present invention will advantageously have the contrast medium present at a concentration sufficient to provide between about 50 milligrams and 500 milligrams of organically bound iodine per milliliter of solution (mg I/ml), more preferably about 100–400 mg/I ml. Further, in accordance with the invention, the solution will generally contain endotoxin at a level exceeding 0.2 EU per 50 mg I (0.2 EU/50 mg I), and often exceeding about 5 EU/50 mgI).

Preferred bulk non-ionic iodinated contrast media to which the invention can be applied are encompassed by the formula:

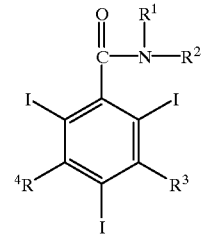

wherein $R^1$ and $R^2$, which may be the same or different, are each a hydrogen atom, an alkyl group, a hydroxylalkyl group or an alkanoyloxyalkyl group and $R^3$ and $R^4$, which may be the same or different, are each a group of the formula—$NR^5Ac$, where $R^5$ is a hydrogen atom, an alkyl group, a hydroxylalkyl group, an alkanoyloxyalkyl group or an alkanoyl group and Ac is an alkanoyl group; a group of the formula—$CH_2NR^5Ac$, where $R^5$ and Ac have the above meanings; or a group

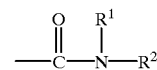

as defined above; each alkyl, hydroxyalkyl or alkanoyl group which is present having up to 6 carbon atoms there being at least one N-hydroxyalkyl and at least two hydroxyl groups in the molecule.

Where the compounds of the invention carry one or more of the group

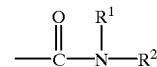

these are preferably mono- or dialkyl and/or hydroxyalkyl groups advantageously having 1–6 carbon atoms in the alkyl portion. Acylamino groups which are preferred include lower aliphatic acylamino groups (advantageously those having 1–6 carbon atoms) which may carry as a further N-substituent an alkyl, hydroxyalkyl or acyloxyalkyl group.

The hydroxyalkyl groups which are present may carry a single hydroxy group, as in the beta-hydroxyethyl group, or more than one hydroxy group as in the dihydroxypropyl or tris-(hydroxymethyl)-methyl group or in the polyhydroxyalkyl portion of hexosamines, pentosamines, and sugar amino-alcohol such as glucosamine or mannosamine or glucamines, e.g. N-methyl glucamine, 1-glucamine or 2-glucamine. Other non-ionic substituents may also be present, for example the aldehyde group as present in glucosamine or one or more acyloxy groups.

The alkyl, hydroxyalkyl and aliphatic acyl groups which are present preferably contain 1–6 carbon atoms. Preferred alkyl groups thus include methyl, ethyl, propyl, butyl and hexyl groups; the methyl group is preferred and an N-methyl substituent may enhance water solubility. The acyl group Ac may for example, be derived from a carboxylic acid or a sulphonic acid.

Preferred acyl groups derived from carboxylic acids, which may be O-attached or N-attached include acetyl, propionyl and butyryl groups, the acetyl group being most preferred. Preferred acyl groups derived from sulphonic acids include alkane sulphonyl groups such as the methane sulphonyl group.

The alkyl, hydroxyalkyl and acyl groups which are present may additionally carry a further non-ionic iodinated hydrocarbon grouping which may carry additional amide groups and, thus, for example, an alkylene, hydroxyalkylene or a diacyl grouping derived from a dibasic acid may be N-bonded at either end to identical iodinated hydrocarbons carrying amide groupings.

Preferred processes employ readily available and inexpensive equipment. Further, once begun, desirable processes can be carried out with minimal additional maintenance. For example, processes of the invention can be conducted in a system which includes a mixing reservoir, e.g. having a volume in the range of 50 L to 1,000 L, and a purification system which includes an in-line pump and an in-line activated carbon filter. The mixing reservoir and the purification system are formed from materials, such as stainless steel, which are both durable and inert to the materials being mixed and/or transfered therein.

The activated carbon filter provides effective, rapid removal of endotoxins from the bulk substance at hand. The separation occurs as a result of the selective binding of endotoxin to the particles of the activated carbon filter. The iodinated, non-ionic contrast media exhibits essentially no affinity for the activated carbon, and thus the endotoxin is effectively separated from bulk contrast media solutions.

The system pump will preferably pass the solution through the purification loop at a rate that will optimize not only the amount of endotoxin that is removed from the solution passing through the filter, but also the volume of solution that is passed through the filter in a given amount of time. Flow rates of between 1 and 10 L/min., more preferably between 2 and 5 L/min., will be typical for processes of the invention.

The system will preferably be operated at a pressure of between 1 psig and 100 psig, more preferably between 5 psig and 15 psig, most preferably about 10 psig. Further, the system will maintain a solution temperature that will allow for the desired separation and which is below the decomposition temperature of the bulk material involved. Preferably, processes of the invention will be operated at a solution temperature of between 15° C. and 35° C., more preferably between 20° C. and 30° C.

The purification system will desirably be allowed to run within the above parameters for a duration sufficient to achieve the desired reduction of endotoxin to acceptable levels. Typically, such runs will last between about 0.5 and about 10.0 hours, more preferably between about 1.5 and about 2.5 hours. Samples can be periodically taken and tested to monitor endotoxin levels, and the process can be discontinued once acceptable levels are achieved.

The end product will be comprised of a solution of contrast medium containing essentially all of the total contrast medium the starting solution, with 90–100% recovery being easily achieved. On the other hand, the product solution will contain the endotoxin at a substantially reduced level as compared to the starting solution (preferably at least 50% reduced), and will more preferably be essentially free from endotoxin (i.e. containing endotoxin at a level of less than about 0.2 EU/50 mgI).

One advantageous feature of the present invention is that, if desired, the product can be taken directly from the inventive process to formulation, filling and terminal sterilization, without the need to recrystallize or otherwise recover the contrast agent in solid form. Such formulation may include, for instance, the incorporation of pharmaceutically acceptable organic and/or inorganic carrier substances, stabilizers such as sodium edetate, calcium disodium edetate, physiologically compatible buffers (see e.g. U.S. Pat. No. 4,863,714), sodium chloride, and the like. For intravenous administration, the contrast agents will typically be used in aqueous medium at concentrations in the range of 50–400 mg I/ml, more typically about 100–400 mg I/ml, with dosages running from about 2 ml to about 500 ml.

In order to promote a further understanding of the present invention and its features and advantages, the following Examples are provided. It will be understood that these Examples are illustrative and not restrictive of the invention.

EXAMPLE

A. Equipment

A purification system was constructed in which a 300 L stainless steel mixing tank, a recirculation pump, and an activated carbon filter were fluidly connected using reinforced silicone tubing. The activated carbon filter was a Cuno Zetacarbon 16 stack filter, available from Cuno Inc.—Process Filtration Products, Arlington Heights, Ill.

B. Preparation of Endotoxin-Contaminated Bulk Contrast Agent

Ioxilan was dissolved in water for injection in the stainless steel tank to prepare a 250 L batch of Ioxilan solution at a concentration of 350 mg I/ml (727 mg IOXILAD/mL). This batch was spiked with Controlled Standard Endotoxin (Endosafe Inc., Charleston, S.C.) to a level of 40 EU/ml, representing 5.7 EU/50 mgI. The tank was then connected to the filtration system as described above.

C. Removal of Endotoxin

The above-described purification system was operated at a tank pressure of 12 psig and a flow rate of about 3.3 L/min. The temperature of the batch was maintained between 20° C. and 30° C. During operation, samples were pulled from the tank initially and at 0.5 hour intervals. These samples were assayed for Ioxilan content (mg I/ml) and endotoxin level (EU/50 mg/I). The endotoxin assays were kinetic turbimetric assays performed using sterile/non-pyrogenic microtiter plates incubated at 37° C. for 1 hour. The onset OD was read at 340 nm, with standards of 50, 5, 2, 0.5, 0.125 and 0.03 EU/ml being used. All standard curves exhibited correlation coefficients of at least −0.995. Spike recoveries of the diluted samples (1:35) were all within 75–100%. Negative controls were negative and positive water controls were about 100%. The averaged results of several identical experiments are shown in Table 1 below, and in FIG. 1. As can be seen, processes of the invention achieved greater than a log reduction in endotoxin level in a relatively short, commercially-feasible period of time. At the same time the potency of the ioxilan in solution remained unchanged. Processes of the invention thus provide for extremely cost-effective means for reducing endotoxin contamination in non-ionic iodinated contrast agents at pre-drug product stages.

TABLE 1

| Time Interval (Hrs) | Endotoxin Level (EU/50 mgI) | Potency (mgI/mL) |
|---|---|---|
| 0 | 5.49 | 357 |
| 0.5 | 2.93 | 356 |
| 0.75 | 2.81 | 360 |
| 1.0 | 2.40 | 359 |
| 1.5 | 1.39 | 357 |
| 2.0 | 1.03 | 355 |
| 2.5 | 0.66 | 357 |
| 3.0 | 0.50 | 356 |
| 3.5 | 0.34 | 359 |
| 4.0 | 0.27 | 357 |
| 4.5 | 0.25 | 357 |
| 5.0 | 0.20 | 361 |
| 5.5 | 0.19 | 356 |
| 6.0 | 0.18 | 356 |
| 6.5 | 0.14 | 357 |

What is claimed is:

1. A process for removing endotoxin from a bulk, non-ionic iodinated contrast medium, comprising:

dissolving the medium in an aqueous starting solution;

passing the solution through a filtration zone containing activated carbon, for a duration and under conditions effective to remove endotoxin from the solution; and recovering after said passing step an aqueous product solution of the medium essentially free from endotoxin.

2. The process of claim 1 wherein the non-ionic contrast medium is of the formula:

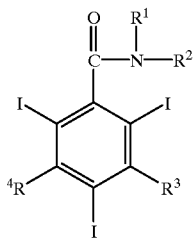

wherein $R^1$ and $R^2$, which may be the same or different, are each a hydrogen atom, an alkyl group, a hydroxylalkyl group or an alkanoyloxyalkyl group and $R^3$ and $R^4$ which may be the same or different, are each a group of the formula—$NR^5Ac$, where $R^5$ is a hydrogen atom, an alkyl group, a hydroxylalkyl group, an alkanoyloxyalkyl group or an alkanoyl group and Ac is an alkanoyl group; a group of the formula—$CH_2NR^5Ac$, where $R^5$ and Ac have the above meanings; or a group

as defined above; each alkyl, hydroxyalkyl or alkanoyl group which is present having up to 6 carbon atoms there being at least one N-hydroxyalkyl and at least two hydroxyl groups in the molecule.

3. The process of claim 2 wherein the non-ionic contrast medium is 5-(N(2,3-dihydroxypropyl) acetamido)N-(2-hydroxyethyl)-N'-(2,3-dihydroxypropyl) 2,4,6-triiodo-isophthalamide.

4. The process of claim 2 wherein said starting solution contains endotoxin at a level exceeding about 0.5 EU/50 mgI, and wherein said product solution contains endotoxin at a level less than 0.2 EU/50 mgI.

5. The process of claim 4 wherein said starting solution contains the contrast medium at a concentration in the range of about 100 mg I/ml to about 400 mg I/ml.

6. The process of claim 5 wherein the contrast medium is 5-(N(2,3-dihydroxypropyl) acetamido)N-(2-hydroxyethyl)-N'-(2,3-dihydroxypropyl) 2,4,6-triiodo-isophthalamide.

7. A process for producing a formulated, non-ionic iodinated contrast medium from an endotoxin-contaminated bulk non-ionic iodinated contrast medium, comprising:

(a) dissolving an amount of a solid, endotoxin-contaminated bulk non-ionic iodinated contrast medium in aqueous solution;

(b) passing said aqueous solution from step (a) through a filtration zone containing activated carbon for a duration and under conditions effective to adsorb essentially all of said endotoxin on said activated carbon and produce a product solution essentially free from endotoxin;

(c) filling the product solution from step (b) into sterilizable containers; and (d) sterilizing filled containers from step (c).

8. The process of claim 2 wherein said passing includes continuously circulating said solution through a circulation loop including said filtration zone, during which said solution has a temperature between about 15° C. and about 35° C.

9. The process of claim 8 wherein said continuously circulating is for a period of time between about 0.5 and about 10 hours.

10. The process of claim 9 wherein said starting solution contains endotoxin at an initial level exceeding about 0.2 EU/50 mgI, and wherein said product solution contains endotoxin at a level less than about 50% of said initial level.

11. The process of claim 9 wherein said starting solution contains endotoxin at an initial level exceeding about 5 EU/50 mgI and said product solution contains endotoxin at a level less than about 0.2 EU/50 mgI.

12. The process of claim 11 wherein said continuously circulating is for a time period between about 1.5 and about 2.5 hours, during which said solution has a temperature between about 20° C. and about 30° C.

13. The process of claim 2 wherein said product solution contains at least about 90% by weight of the contrast medium dissolved in said starting solution.

14. The process of claim 7 wherein during said passing said solution has a temperature between about 15° C. and about 35° C.

15. The process of claim 14 wherein said aqueous product solution contains at least about 90% by weight of said amount of contrast medium in said dissolving step.

16. The process of claim 7 wherein said dissolving provides said solution containing endotoxin at an initial level exceeding about 0.2 EU/50 mgI, and said product solution contains endotoxin at a level less than about 0.2 EU/50 mgI.

17. The process of claim 7 wherein said dissolving provides said solution containing endotoxin at an initial level exceeding about 5 EU/50 mgI, and said product solution contains endotoxin at a level less than about 50% of said initial level.

18. The process of claim 7 wherein said passing includes continuously circulating said solution through a circulation loop including said filtration zone for a period of time between about 0.5 and about 10 hours, during which said solution has a temperature of between about 15° C. and about 35° C.

19. The process of claim 17 wherein said continuously circulating is for a period of time between 1.5 and about 2.5 hours, during which said solution has a temperature of between about 20° C. and about 30° C.

20. The process of claim 7 wherein said contrast medium is 5-(N(2,3-dihydroxypropyl) acetamido)N-(2-hydroxyethyl)-N'-(2,3-dihydroxypropyl) 2,4,6-triiodo-isophthalamide.

* * * * *